(12) United States Patent
Irion et al.

(10) Patent No.: US 8,012,158 B2
(45) Date of Patent: Sep. 6, 2011

(54) DEVICE FOR FRAGMENTING SUBSTANCES

(75) Inventors: Klaus M. Irion, Liptingen (DE); Clemens Rebholz, Uhldingen-Mühlhofen (DE)

(73) Assignee: Karl Storz GmbH & Co. KG (DE)

( * ) Notice: Subject to any disclaimer, the term of this patent is extended or adjusted under 35 U.S.C. 154(b) by 1610 days.

(21) Appl. No.: 11/328,712

(22) Filed: Jan. 10, 2006

(65) Prior Publication Data

US 2006/0142754 A1 Jun. 29, 2006

Related U.S. Application Data

(63) Continuation of application No. PCT/EP2004/007608, filed on Jul. 9, 2004.

(30) Foreign Application Priority Data

Jul. 11, 2003 (DE) .................. 103 31 694

(51) Int. Cl.
*A61B 17/22* (2006.01)
(52) U.S. Cl. ...................................... 606/128
(58) Field of Classification Search .................. 600/439, 600/471; 604/22; 606/127–128, 167, 169–170, 606/107, 166
See application file for complete search history.

(56) References Cited

U.S. PATENT DOCUMENTS

| | | | | |
|---|---|---|---|---|
| 3,593,551 A | * | 7/1971 | Roth et al. | 72/56 |
| 3,927,675 A | * | 12/1975 | Pohlman et al. | 606/128 |
| 4,605,003 A | | 8/1986 | Oinuma et al. | |
| 5,103,556 A | | 4/1992 | Filip et al. | |
| 5,372,124 A | * | 12/1994 | Takayama et al. | 600/106 |
| 5,425,735 A | | 6/1995 | Rosen et al. | |
| 5,433,731 A | * | 7/1995 | Hoegnelid et al. | 607/5 |
| 5,540,702 A | | 7/1996 | Walz | |
| 6,413,230 B1 | | 7/2002 | Haupt et al. | |
| 6,736,784 B1 | * | 5/2004 | Menne et al. | 601/2 |

FOREIGN PATENT DOCUMENTS

| | | |
|---|---|---|
| DE | 195 10 920 | 9/1996 |
| EP | 0 640 316 | 3/1995 |
| JP | 61217147 | 9/1986 |
| WO | WO 93/11711 | 12/1992 |

OTHER PUBLICATIONS

International Preliminary Report on Patentability; 5 pages.

* cited by examiner

*Primary Examiner* — Anhtuan T Nguyen
*Assistant Examiner* — Ashley Cronin
(74) *Attorney, Agent, or Firm* — St. Onge Steward Johnston & Reens LLC

(57) ABSTRACT

A device for fragmenting substances comprises a probe having an elongate probe shaft on the distal end of which a probe head is arranged, said probe head comprising an electrohydraulic converter with which electrical energy, delivered via the probe shaft from the proximal direction, is converted in shock-like manner into mechanical kinetic energy, said converter comprising a housing which accommodates a liquid chamber and a shock-transmitting element which is designed as a piston and which can be moved in the longitudinal direction of the housing from a proximal end position to a distal end position, the distal end position being defined by an abutment on the housing, which abutment is struck by a counter-abutment arranged on the shock-transmitting element. The abutment and the counter-abutment are designed in such a way that, during its movement from the proximal end position to the distal end position, the counter-abutment comes directly into contact with the abutment, and the shock-transmitting element is moved back again to the proximal end position essentially by the impact on the abutment.

25 Claims, 5 Drawing Sheets

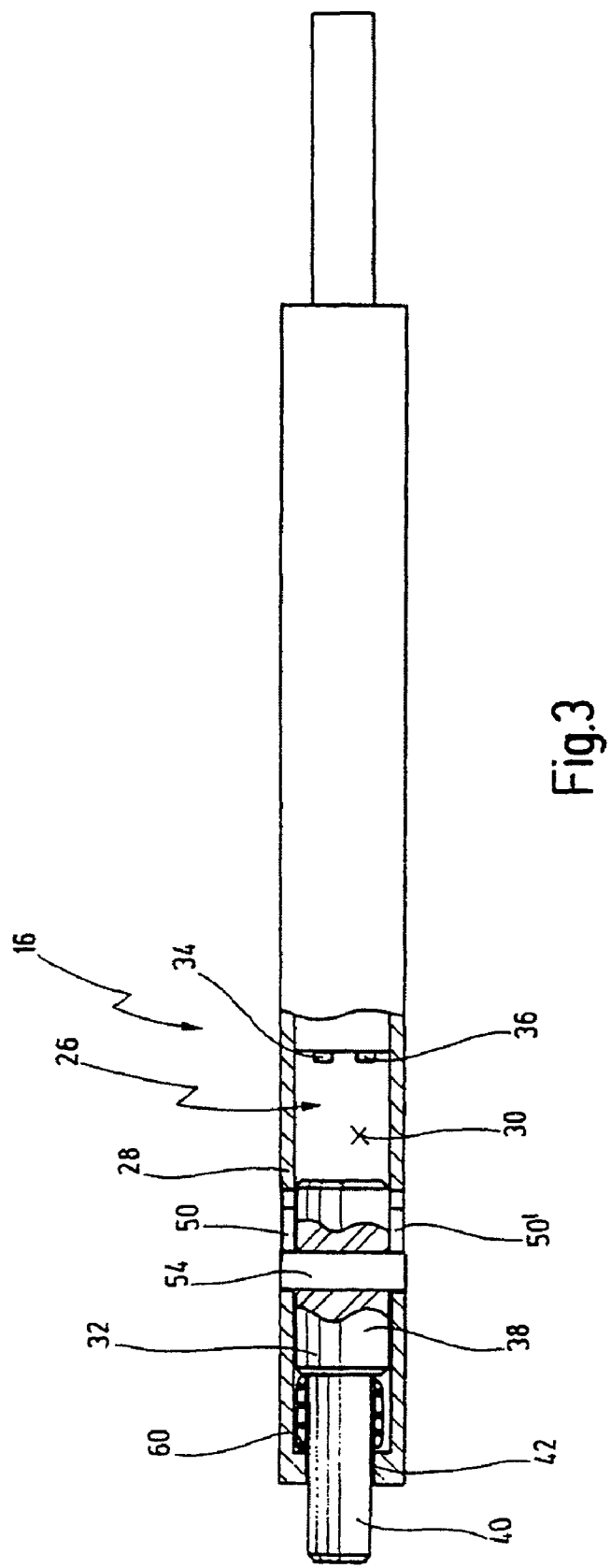

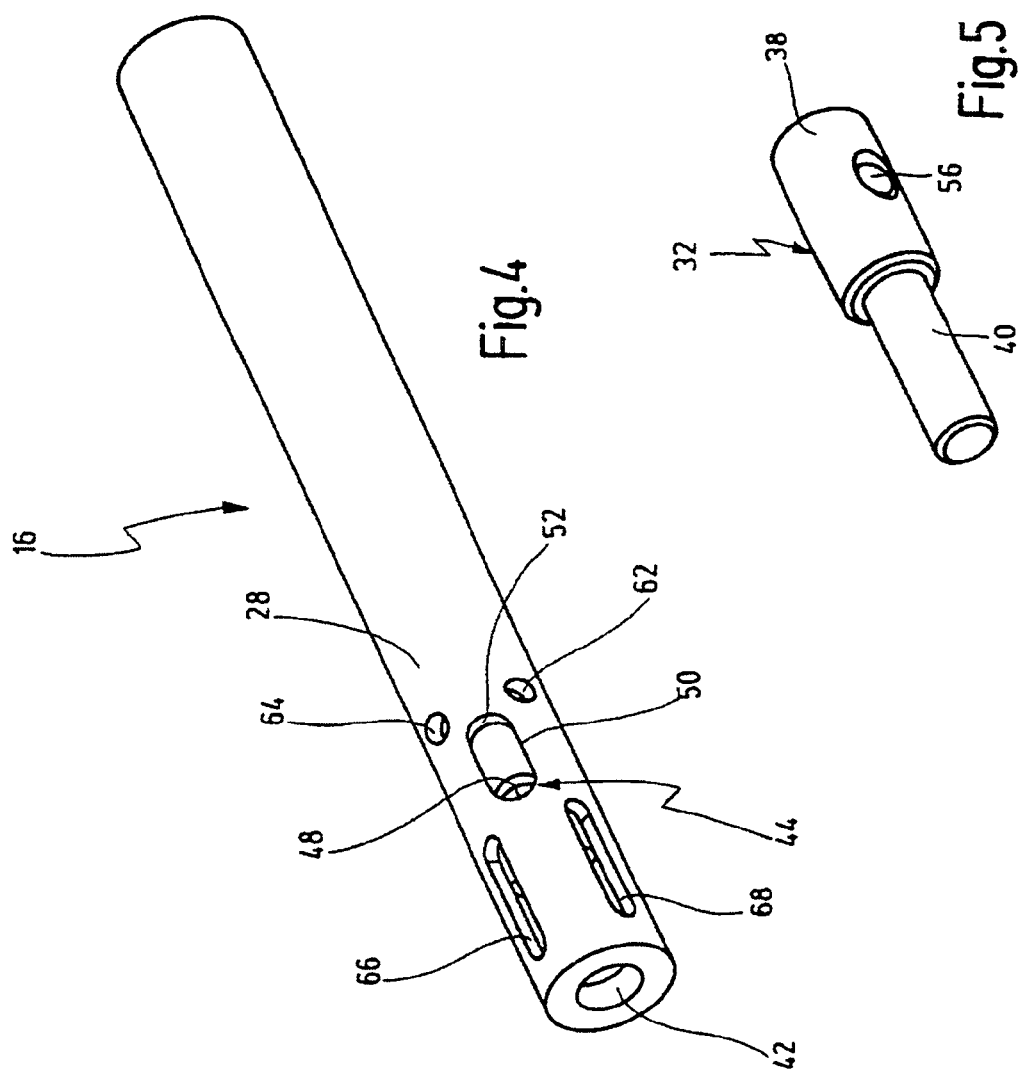

DEVICE FOR FRAGMENTING SUBSTANCES

CROSS-REFERENCE TO RELATED APPLICATIONS

The present application is a continuation of pending International Patent Application PCT/EP2004/007608 filed on Jul. 9, 2004 which designates the United States, and which claims priority of German patent application 103 31 694.9 filed on Jul. 11, 2003.

BACKGROUND OF THE INVENTION

The invention generally relates to a device for fragmenting substances.

Such a device is used in medicine in the context of electro-hydraulic lithotripsy for fragmentation of hard tissue and of concretions, for example intracorporeal stones, for example kidney stones, urethral stones, bladder stones, gall stones, salivary stones, etc., bone, cartilage, lens material in the eye, bone cement, thrombi, deposits and calcifications.

Moreover, such a device can also be used for stimulation of tissue.

Although the invention is described below with reference to its medical applications, a device of the type mentioned at the outset can also be employed in technical and industrial sectors, for example for fragmentation of lime deposits in pipeline systems.

The electro-hydraulic lithotripsy (EHL) probe known from document U.S. Pat. No. 5,425,735 comprises an electro-hydraulic converter arranged in the probe head. The electro-hydraulic converter has two electrodes which are immersed in a liquid in a liquid chamber within the housing of the electro-hydraulic converter. Arranged distal by and at a slight distance from the electrodes, there is a shock-transmitting element designed as a piston which can move axially in the housing from a proximal end position (rest position) to a distal end position. By applying a current impulse to the two electrodes, the electrical short circuit brings about an explosion-like formation of cavitation bubbles in the conductive liquid in the liquid chamber, and these cavitation bubbles lead to an shock-like pressure wave which moves the shock-transmitting element in shock-like manner in the distal direction away from its proximal rest position, such that a distal end face of the shock-transmitting element can impact the substance that is to be fragmented, in order to crush this substance.

The device known from the aforementioned document to this extent represents an improvement on conventional EHL probes in which no shock-transmitting element is provided and in which the fragmentation is brought about with the aid of the pressure wave that arises as a result of the explosion-like spark discharge on the electrodes. Such a device is known from EP-A-0 640 316, for example. However, the pressure waves acting not just axially but in all directions have the disadvantage of causing soft-tissue trauma, for example as a result of burns caused by sparks during short-circuiting of the electrodes and mechanical defects such as perforations.

The shock-transmitting element of the EHL probe known from U.S. Pat. No. 5,425,735 avoids this problem, since the pressure waves propagating in all directions are channeled axially in the liquid chamber. The shock-transmitting element is moved from the proximal end position to the distal end position by the explosion-like propagation of the pressure waves (shock waves), the distal end position being defined by an abutment which is arranged on the housing of the converter and which, in the known device, is formed by a radial annular surface in the area of the distal end of the housing. Provided on the shock-transmitting element there is a counter-abutment which is designed in the form of a radial annular surface in the area of the proximal end of the shock-transmitting element.

Arranged between the counter-abutment and the abutment there is a compression spring which bears at its distal end on the annular surface on the housing and bears at its proximal end on the annular surface on the shock-transmitting element. The compression spring is thus coupled into the running path of the counter-abutment. The compression spring has the purpose of moving the counter-abutment back again from the distal end position to the proximal end position.

Such a design of a restoring mechanism for the shock-transmitting element has disadvantages, however. Since the compression spring is arranged within the entire possible stroke range of the shock-transmitting element, the following situations may arise.

If the spring is hard, a situation may arise in which the shock-transmitting element executes only a partial stroke of its maximum path of movement between the proximal end position and the distal end position, such that the shock-transmitting element strikes against a "soft" abutment. It is not then possible, however, to optimally accelerate the shock-transmitting element and thereby transmit the kinetic energy of the shock-transmitting element to the fragmentable substance as shock-like as possible and starting from the maximum speed.

If the spring is soft, on the other hand, so that the shock-transmitting element can run as far as the distal end abutment, the spring nevertheless has to be completely compressed, as a result of which part of the kinetic energy imparted to the shock-transmitting element by the pressure wave is dissipated by the spring, which leads to deceleration of the shock-transmitting element. In this case too, therefore, there is no optimum shock-like transfer of energy to the substance that is to be fragmented.

Moreover, DE-A-195 10 920 discloses a device for crushing concretions in the medical sector, said device having a probe whose distal end points in the direction of a concretion that is to be crushed, and whose proximal end is accommodated in a housing in a guide. This housing is thus arranged at the proximal end of the probe shaft, such that the shock wave is generated outside the body. Moreover, the shock wave is not generated directly by means of an electro-hydraulic converter but instead by means of an electromagnetic linear motor.

At the proximal probe end, the probe shaft has an impact surface which is impacted by a mass accelerated in the electromagnetic field in order to introduce impulses into the probe, which impulses are conveyed through the probe in the direction of the concretion that is to be fragmented. At an inlet of a probe guide lying in an abutment surface, the impact surface of the probe forms a defined starting state to which the probe can be returned after each shock impulse. The return of the probe takes place via a damping element in the distal area of the probe, which element, although not being completely compressed, nevertheless represents a soft abutment for the probe, which represents the shock-transmitting element. This is because the action of the damping element is a deceleration of the probe.

A further disadvantage of this known device lies in the fact that the shocks are generated outside the body. Because of the probe shaft length, which has to transmit the shock, and the guiding thereof in an endoscope, for example, or in a hollow organ, friction occurs which greatly attenuates the mechanical shock and thus reduces the fragmentation effect. In certain applications, the probe shaft moreover adopts a curved course inside the body, as a result of which the energy dissipation of the shock inside the probe is further intensified. In addition, the probe shaft cannot be made sufficiently flexible to maintain its suitability for shock transmission.

SUMMARY OF THE INVENTION

The object of the invention is to develop a device of the type mentioned at the outset in such a way as to improve the transmission of the movement impulse of the shock-transmitting element to the substance that is to be fragmented.

According to an aspect of the invention, a device for fragmenting substances is provided, comprising a probe having an elongate probe shaft having a distal end and a proximal end, a probe head arranged at the distal end, the probe head comprising an electro-hydraulic converter with which electrical energy, delivered via the probe shaft, is converted in shock-like manner into mechanical kinetic energy. The electro-hydraulic converter has a housing having a longitudinal direction, which accommodates a liquid chamber and a shock-transmitting element designed as a piston and moveable in the longitudinal direction of the housing from a proximal end position into a distal end position. The distal end position being defined by an abutment on the housing, toward which abutment a counter-abutment runs, which is arranged on the shock-transmitting element, the abutment and the counter-abutment being designed in such a way that, during a movement of the shock-transmitting element from the proximal end position to the distal end position, the counter-abutment comes directly into contact with the abutment. The shock-transmitting element is moved back again to the proximal end position essentially by the impact of the counter-abutment on the abutment.

Accordingly, in the device according to the invention, the aim is to keep the running path of the counter-abutment to the abutment free, i.e. a spring is not coupled into the direct running path as in the known device, with the result that the counter-abutment of the device according to the invention comes directly into contact with the abutment and therefore makes a hard contact rather than a soft contact with the abutment. As the restoring mechanism for the shock-transmitting element of the device according to the invention, it is therefore not necessary to use the force of a spring against which the shock-transmitting element has to run upon its movement from the proximal end position to the distal end position and give off energy to said spring; instead, the shock-transmitting element is moved back to the proximal end position by the fact that the counter-abutment impacts hard on the abutment and is thereby "reflected" on the latter. This therefore avoids a situation where a considerable part of the energy is withdrawn from the shock-transmitting element, during its movement from the proximal end position to the distal end position, by an energy accumulator, for example a spring. The expression "hard" abutment is to be understood as meaning that the counter-abutment experiences, on the abutment, an in the physical sense elastic impact in which essentially no deformation work is performed. In this way, the fragmentation action of the device according to the invention is improved.

In a preferred embodiment, the shock-transmitting element is held in the proximal end position by means of a holding mechanism which withdraws essentially no kinetic energy from the shock-transmitting element during its movement from the proximal end position to the distal end position.

In the device according to the invention, in contrast to the prior art, a holding mechanism for the shock-transmitting element is provided in the proximal end position, which advantageously ensures that the shock-transmitting element always starts its movement stroke from the direction of the proximal end position. However, this holding mechanism provided according to the invention is designed in such a way that it withdraws essentially no kinetic energy from the shock-transmitting element, as a result of which the mechanical shock transmission is not impaired by the holding mechanism.

In another preferred embodiment, the holding mechanism comprises a spring which is designed in such a way that its maximum possible spring travel is greater than the path of the shock-transmitting element between the proximal end position and the distal end position.

It is true that in this preferred embodiment a spring is provided, similarly to the known device, but this spring simply has the object of keeping the shock-transmitting element in the proximal end position. In contrast to the prior art, the spring is designed in such a way that it withdraws essentially no kinetic energy from the shock-transmitting element during the latter's movement from the proximal end position to the distal end position, because its maximum spring travel is greater than the movement stroke of the shock-transmitting element. For example, the maximum spring travel can be more than 1.2 times the stroke, preferably more than 2 times the stroke, of the shock-transmitting element.

In this connection, it is preferable if the spring is a compression spring whose length is greater than the path of the shock-transmitting element between the proximal end position and the distal end position.

In the known device, by contrast, the length of the compression spring is equal to the maximum movement stroke of the shock-transmitting element which in the present invention has the advantage of an essentially unbraked movement of the shock-transmitting element between the proximal end position and the distal end position.

In another preferred embodiment, the spring is arranged around a distal portion of the shock-transmitting element and bears at its distal end on the housing and at its proximal end on a shoulder of the shock-transmitting element, without lying in the running path of the counter-abutment.

In contrast to the arrangement of the spring in the known device in which in fact the spring is arranged in the running path between the counter-abutment and the abutment, the present arrangement of the spring is advantageous because the counter-abutment can thus impact freely against the distal hard abutment on the housing, thereby permitting optimal transmission of the impulse to the substance that is to be fragmented.

Alternatively or additionally to the aforementioned spring, the holding mechanism can preferably hold the shock-transmitting element in the proximal end position by means of magnetic force.

An advantage of this is that a magnetic holding mechanism requires less structural space than does a spring, as a result of which the probe of the device according to the invention can be designed with very small dimensions in its distal area, which is advantageous for applications of the device for fragmentation of stones in the ureter.

In another preferred embodiment, the counter-abutment is designed as a lateral projection which engages in a slide track in the wall of the housing, the distal end thereof forming the abutment on the housing.

This construction represents a structurally advantageous and simple possibility of designing counter-abutment and abutment in such a way that the counter-abutment runs freely toward the abutment on the housing and can be "reflected" thereon. The slide track can, for example, be a recess in the wall of the housing.

It is also preferable if the slide track is delimited at the proximal end in order to define the proximal end position of the shock-transmitting element.

In this way, the proximal end position of the shock-transmitting element is at the same time also defined by the same slide track, as a result of which the outlay in terms of construction is still further reduced, because no additional abutment for the proximal end position is needed in the form of a separate component part.

The aforementioned slide track can for example be in the form of an oblong hole which extends radially through the wall of the housing or in the form of an internal depression in the housing wall.

In another preferred embodiment, the aforementioned lateral projection is formed by a pin which extends transversely through the shock-transmitting element and which at opposite ends engages in a respective slide track in the wall of the housing.

A stable counter-abutment is formed by such a pin, and the fact that the pin is guided at at least two ends in a respective slide track in the wall of the housing means that the shock-transmitting element is also guided in the housing of the converter in a manner secure against jamming, thereby avoiding increased friction or at least jamming of the shock-transmitting element in the housing, which likewise leads to unbraked transmission of shock to the substance that is to be fragmented.

In another preferred embodiment, the stroke of the shock-transmitting element between the proximal end position and the distal end position lies in the range from approximately 0.2 to approximately 2 mm, preferably from approximately 0.4 to approximately 1.5 mm.

This measure advantageously contributes to improved transmission of the shock-like kinetic energy of the shock-transmitting element to the substance that is to be fragmented, because the shortness of the path of movement largely avoids loss of kinetic energy in the movement from the proximal end position to the distal end position.

In other preferred embodiments, the speed of the shock-transmitting element is at least 2 m/s, preferably at least 5 m/s, more preferably at least 15 m/s, and/or the repetition frequency of the movement of the shock-transmitting element from the proximal end position to the distal end position is at least 2 Hz, preferably at least 15 Hz.

In another preferred embodiment, at least one delivery line for a liquid leads into the liquid chamber of the electro-hydraulic converter.

An advantage of this is that any loss of liquid in the liquid chamber can be compensated even during use of the device in the body, as a result of which an optimal function of the electro-hydraulic converter is ensured at all times.

It is preferable in this case if the at least one delivery line extends through the probe shaft, and/or the at least one delivery line is formed by at least one opening in the wall of the housing of the converter, and/or the at least one delivery line is formed by at least one through-opening in the shock-transmitting element.

The provision of the at least one delivery line through at least one opening in the wall of the housing of the converter and/or through at least one through-opening in the shock-transmitting element has the advantage that the probe itself can be of a very simple design, since it is possible to dispense with a delivery line from the proximal direction. Since intracorporeal treatment of urinary stones, for example, always take place in a liquid environment, this liquid in the body can then pass through the at least one opening in the wall of the housing or in the shock-transmitting element and into the liquid chamber.

In the case where the at least one delivery line is formed by at least one opening in the wall of the housing of the converter, the at least one opening is preferably arranged distally from a portion of the shock-transmitting element which portion permits passage of liquid into the liquid chamber but prevents penetration of voltage sparks.

In this embodiment, the liquid can pass into the housing at a site distal from the liquid chamber and, for example, can pass through a certain clearance between the shock-transmitting element and the housing of the converter into the liquid chamber. This advantageously avoids a situation in which the ignition sparks of the electro-hydraulic converter extend outward from the housing of the converter and may injure the patient.

In another preferred embodiment, the probe shaft is flexible.

An advantage of this is that the device according to the invention can also be introduced into bodily passages which are not straight, for example, in urological treatment, into the ureter.

In another preferred embodiment, the probe head has, in its proximal area, a stiffening part, for example in the form of a metal tube.

This can advantageously ensure that the shock effect is oriented in the distal direction and not in the proximal direction.

It is preferable here if the probe head has a stiffening part along its entire length.

An advantage of this is that a rebound of the probe in the proximal direction is prevented.

In another preferred embodiment, the probe head has a diameter of less than approximately 5 mm, preferably less than approximately 2 mm, preferably less than approximately 1.5 mm.

An advantage of this is that the device according to the invention can also be introduced into very narrow bodily ducts for fragmentation of substances or for stimulation of tissue.

In another preferred embodiment, the probe is integrated in a catheter.

It is preferable here if the catheter additionally has at least one lumen for the delivery and/or removal of irrigation liquid, and/or additionally has a lumen for the passage of a miniaturized endoscope.

In another preferred embodiment, an acoustic sensor is present which detects the acoustic signal of the ignition of the electro-hydraulic converter and of the impact of the shock-transmitting element on the substance.

An advantage of this is that the acoustic signal received by the sensor can be used to differentiate whether the shock-transmitting element has struck a hard substance, such as a stone in the body, or has struck soft tissue. The impact of the shock-transmitting element on a stone can in fact be distinguished acoustically from an impact of the element against soft tissue. The acoustic sensor can be arranged at the proximal end of the probe shaft and/or on the surface of a patient's body.

Further advantages and features will become apparent from the following description and from the attached drawing.

It will be appreciated that the aforementioned features and those still to be mentioned below can be used not only in the respectively cited combination but also in other combinations or on its own, without departing from the scope of the present invention.

BRIEF DESCRIPTION OF THE DRAWINGS

An illustrative embodiment of the invention is depicted in the drawing and is described in greater detail below with reference to this drawing, in which:

FIG. 3 shows the probe head in FIG. 2 in a second operating position;

FIG. 4 shows a perspective view of a housing of the electro-hydraulic converter according to FIGS. 2 and 3 on its own;

FIG. 5 shows a perspective view of a shock-transmitting element of the electro-hydraulic converter according to FIGS. 2 and 3 on its own.

DETAILED DESCRIPTION OF A PREFERRED EXEMPLARY EMBODIMENT

Figure 1:
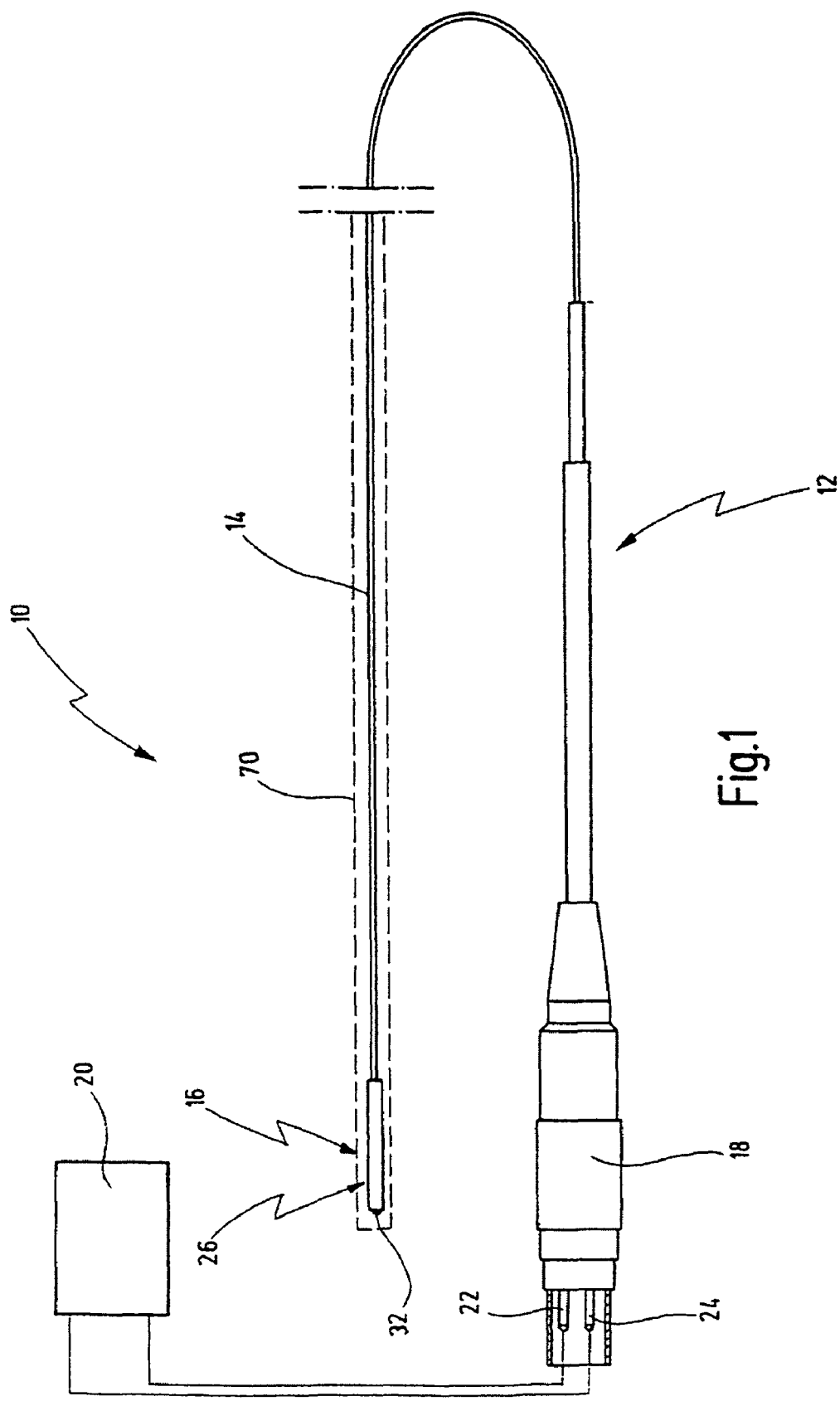
FIG. 1 shows an overall view of a device for fragmenting substances.

A device for fragmenting substances is shown in FIG. 1 and is indicated by the general reference number 10.

The device 10 can be used for lithotripsy of urinary calculi in the bladder, urethra and kidneys, or of gall stones or bile duct stones. The device 10 can additionally be used for lithotripsy of salivary stones. Further applications of the device 10 are the treatment of vascular occlusions in cases of calcification and thrombi, or also stimulation or pressure wave therapy in orthopedics, for example for treatment of tennis elbow. The device 10 can also be used for removing bone cement or for removing the lens from the eye.

The device 10 can also be used for technical purposes, for example for removing lime deposits from pipeline systems.

The device 10 comprises a probe 12 having an elongate probe shaft 14 which, in the illustrative embodiment shown, is flexible and has a probe head 16 at the distal end of the probe shaft 14.

At the proximal end of the probe shaft 14, the probe 12 has a connector housing 18 via which the probe 12 can be connected to an electrical power source 20. The proximal end of the connector housing 18 is provided for this purpose with contacts 22 and 24 to which a cable plug (not shown here) can be attached for connection to the electrical power source 20. Starting from each of the contacts 22 and 24, thin and flexible current-conducting wires (not shown in the drawing) extend through the probe shaft 14. These wires lead to the probe head 16.

Details of the probe 12 are described in more detail below also with reference to FIGS. 2 through 5.

The probe head 16 contains an electro-hydraulic converter 26 with which electrical energy delivered via the probe shaft 14 from the proximal direction is converted in shock-like manner into mechanical kinetic energy via a short circuit. The converter 26 comprises a housing 28 in which a liquid chamber 30 filled with conductive liquid is arranged. The housing 28 also accommodates a shock-transmitting element 32. Two electrodes 34 and 36 are submerged in the liquid chamber 30 and, via the aforementioned current-carrying wires in the probe shaft 14, these two electrodes can receive voltage impulses generated by the electrical power source 20. When the electrodes 34 and 36 receive a current impulse, cavitation bubbles form instantaneously in the liquid in the liquid chamber 30 via the short circuit, and these cavitation bubbles lead to an explosion-like increase in pressure in the liquid chamber 30.

Figure 2:
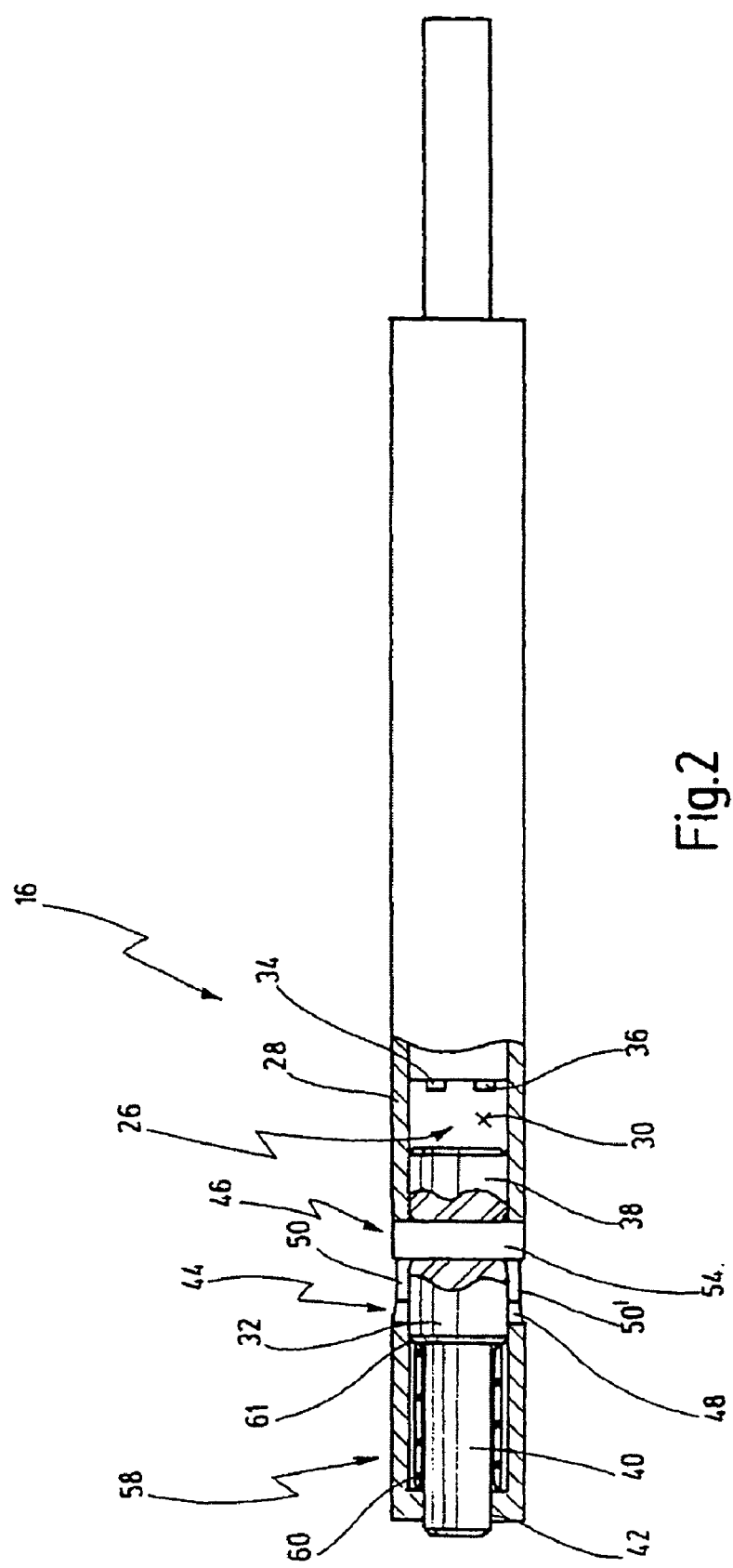
FIG. 2 shows a probe head of the probe of the device in FIG. 1, partly in longitudinal section and on a greatly enlarged scale, in a first operating position.

The shock-transmitting element 32 is movable, in the longitudinal direction of the housing 28 of the electro-hydraulic converter 26, from a proximal end position shown in FIG. 2 to a distal end position shown in FIG. 3, this movement being caused by the explosion-like increase in pressure in the liquid chamber 30 after a voltage impulse acts on the electrodes 34 and 36.

The shock-transmitting element 32 has a proximal portion 38 having an outer circumference which corresponds approximately to the inner circumference of the housing 28 and has a slight clearance in relation to the latter. The proximal portion 28 is adjoined by a distal portion 40 of the shock-transmitting element 32 which has a smaller diameter than the proximal portion 38 and which can protrude distally through a distal opening 42 from the housing 28 when the shock-transmitting element moves from the proximal end position to the distal end position.

The distal end position of the shock-transmitting element 32 is defined by a hard abutment 44 on the housing 28 toward which a counter-abutment 46 of the shock-transmitting element 32 runs, which is arranged on the shock-transmitting element 32, which counter-abutment 46 is designed as a lateral projection on the element 32.

The hard abutment 44 on the housing 28 is formed by a distal end 48 of a slide track 50, the latter being designed in the form of an oblong hole in the housing 28 of the electro-hydraulic converter 26. On the hard abutment 44, the shock-transmitting element 32 experiences a fully elastic impact when the counter-abutment 46 strikes against the abutment 44.

A proximal end 52 of the slide track 50 defines the proximal end position of the shock-transmitting element 32.

Lying diametrically opposite the slide track 50 there is a second slide track 50', likewise in the form of an oblong hole formed on the housing 28.

The counter-abutment 46 of the shock-transmitting element 32 is designed in the form of a pin 54 which is inserted into a bore 56 in the proximal portion 38 of the shock-transmitting element 32 otherwise designed as a solid body. The pin 54 protrudes beyond the proximal portion 38 of the shock-transmitting element 32 on both sides and engages accordingly in the slide track 50 and the slide track 50', as a result of which the shock-transmitting element 32 is guided in the slide tracks 50 and 50'.

As will be seen from FIGS. 2 and 3, the running path of the counter-abutment 46 to the abutment 44 is free, such that the counter-abutment 46 in the distal end position of the shock-transmitting element 32 comes directly into hard contact with the abutment 44. Upon activation of the electrodes 34 and 36 with a current impulse and the associated explosion-like increase in pressure in the liquid chamber 30, the shock-transmitting element 32 is moved in shock-like manner from its proximal end position shown in FIG. 2 into the distal end position shown in FIG. 3, where the counter-abutment 46 strikes hard against the abutment 44 and, because of this collision, the shock-transmitting element 32 experiences a fully elastic impact and is "reflected" from the end position shown in FIG. 3 back to the proximal end position according to FIG. 2.

Figure 6:
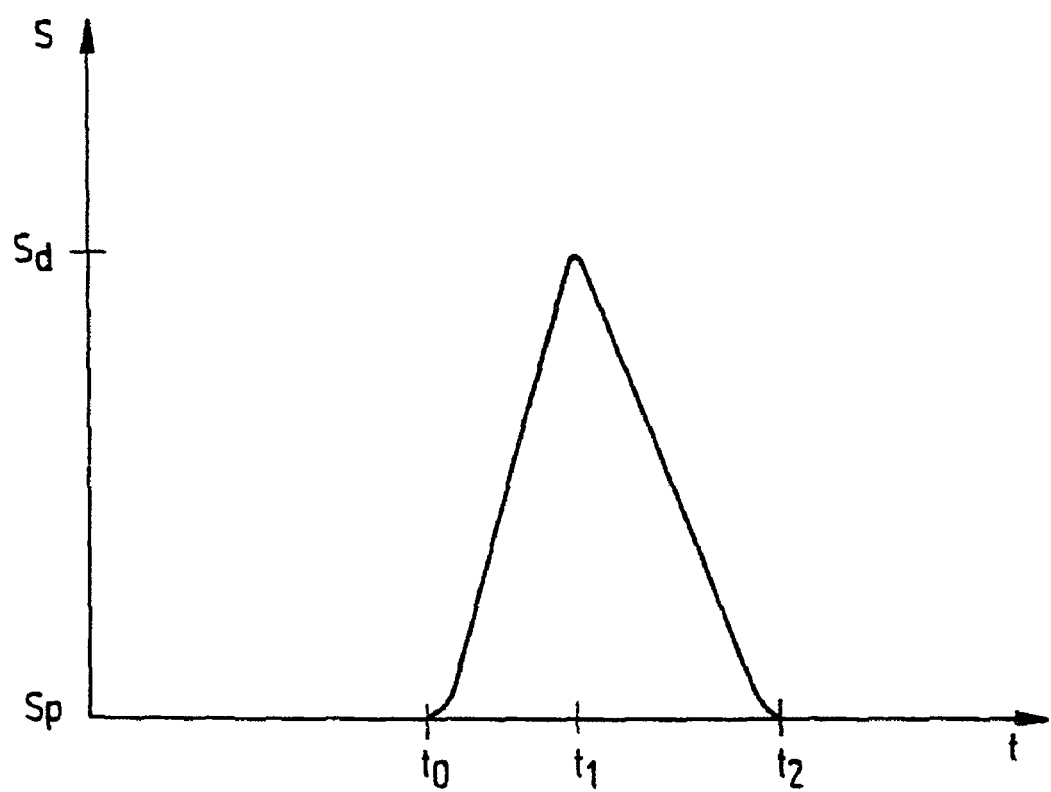
FIG. 6 shows a path/time diagram of the movement of the shock transmitting element during the operation of the device.

FIG. 6 shows a path/time diagram of the course of the movement, in which the time t is plotted on the x axis and the path s of the shock-transmitting element 32 is plotted on the y axis. At the time t0, the shock-transmitting element 32 is set suddenly in movement from the proximal end position sp by ignition of the electrodes 34 and 36 and thus moves with high and above all constant speed, i.e. without braking, to the distal end position sd, as can be seen from the linear rise in the movement curve. In the distal end position sd at the time t1, in which the counter-abutment 46 strikes the abutment 44, a reversal of movement of the element 32 takes place with the same or almost the same speed, as can be inferred from the symmetry of the movement curve about the time t1. At the time t2, the element 32 has once again reached the proximal end position sp.

In a test, a probe was used whose shock-transmitting element 32 has a defined stroke sp-sd of 0.85 mm, where a speed of the element 32 to the abutment 44 of 11.8 m/s was measured.

In order to keep the shock-transmitting element 32 in the proximal end position according to FIG. 2 prior to each ignition of the electrodes 34 and 36, a holding mechanism 58 is provided in the housing 28 and is designed such that, upon movement of the shock-transmitting element 32 from the proximal end position to the distal end position, it withdraws essentially no kinetic energy from the shock-transmitting element 32.

The holding mechanism 58 comprises a spring 60 which is designed such that its maximum spring travel is greater than the path of the shock-transmitting element 32 from the proximal end position to the distal end position. In the illustrative embodiment shown, this is achieved by the fact that the spring 60 is designed as a compression spring whose length is greater than the stroke of the shock-transmitting element 32 between the proximal and distal end positions, i.e. the length of the spring 60 is greater than the length of the slide tracks 50 and 50' in which the counter-abutment 46 runs.

The spring 60 is arranged around the distal portion 40 of the shock-transmitting element 32 and its distal end bears on the housing 28 and its proximal end on a shoulder 61 between the distal portion 40 and the proximal portion 38 of the shock-transmitting element 32.

As will be seen from FIGS. 2 and 3, the spring 60 does not lie in the running path of the counter-abutment 46 to the abutment 44, as a result of which the shock-transmitting element 32 runs, without braking, toward the hard abutment 44 and can return to the proximal end position as a consequence of an almost complete reversal of impulse.

Additionally and alternatively to the spring 60, the shock-transmitting element 32 can also be held in the proximal end position according to FIG. 2 by means of magnetic force. In this case, it is additionally possible to provide a trigger mechanism for the magnetic force, which trigger mechanism switches off the magnetic holding force in synchrony with the ignition of the electrodes 34 and 36 and switches it on again after a time interval corresponding to the time needed by the shock-transmitting element 32 to get from the proximal to the distal end position and from there back to the proximal end position.

The stroke of the shock-transmitting element 32 between the proximal end position and the distal end position, which is predetermined by the length of the slide track 50 or slide track 50', lies in the range from approximately 0.2 to 2 mm, preferably approximately 0.4 to approximately 1.5 mm. The stroke of the shock-transmitting element 32 is therefore very short.

The speed of the shock-transmitting element 32 from the proximal to the distal end position is at least 2 m/s, preferably at least 5 m/s, more preferably at least 15 m/s.

The repetition frequency of the movement of the shock-transmitting element 32 from the proximal end position to the distal end position is at least 2 Hz, preferably at least 15 Hz, such that a sufficient repetition rate of the shock-like movement of the shock-transmitting element 32 is obtained.

At least one delivery line for a liquid leads into the liquid chamber 30 of the electro-hydraulic converter 26, and, in the illustrative embodiment shown, several delivery lines are formed by openings distributed about the circumference, of which four openings 62 to 68 can be seen in FIG. 4, formed in the wall of the housing 28.

Whereas the openings 66 and 68 are arranged distally from the proximal portion 38 of the shock-transmitting element 32, the openings 62 and 64 are also located at a site lying distally from the liquid chamber 30, so that, upon ignition of the electrodes 34 and 36, penetration of the ignition sparks from the housing 28 is avoided.

Additionally or alternatively, liquid can also be delivered into the liquid chamber 30 from the proximal direction via the probe shaft 14, or through bores in the shock-transmitting element 32.

The liquid entering through the openings 62 to 68 is thus conveyed into the liquid chamber 30 in such a way that a slight lateral clearance is present between the proximal portion 38 of the shock-transmitting element 32 and the housing 28, through which clearance it is possible for liquid to pass, while penetration of ignition sparks is avoided. Alternatively to this clearance, and as has already been mentioned, bores can also be provided in the shock-transmitting element 32 for the purpose of conveying the liquid from the distal end in the proximal direction into the liquid chamber 30.

As will be seen from FIGS. 2 and 3, the probe head 16 comprises, in its proximal area, a stiffened part, for example in the form of a metal tube, as the housing 28 of the electro-hydraulic converter 26 extends in the proximal direction very much farther than would be necessary on the basis of the position of the electrodes 34 and 36. The stiffening of the probe head 16 in the proximal area ensures that the shock-like impulse upon ignition of the electrodes 34 and 36 acts in the distal direction and not in the proximal direction.

A rebound of the probe 12 in the proximal direction is also reduced or even avoided by this means.

According to FIG. 1, the probe 12 is integrated in a catheter 70 which is only outlined in the drawing and which comprises at least one lumen for the delivery and/or removal of irrigation liquid and additionally one lumen for passage of a miniaturized endoscope.

The probe head is in particular of a miniaturized design and has a diameter of less than approximately 5 mm, preferably less than approximately 2 mm, more preferably less than approximately 1.5 mm, thereby permitting its integration into a catheter.

Moreover, an acoustic sensor can be provided which is arranged for example in the connector housing 18 of the probe 12 and which detects the acoustic signal of the short circuit of the electrodes 34 and 36 and the impact of the shock-transmitting element 32 on the substance that is to be fragmented. Since the impact of the shock-transmitting element 32 on, for example, a calculus in the body is different than the impact on soft tissue, the acoustic sensor permits differentiation in respect of the target substance that is to be treated.

What is claimed is:

1. A device for fragmenting substances, comprising:
a probe having an elongate probe shaft having a distal end and a proximal end, a probe head arranged at said distal end, said probe head comprising an electro-hydraulic converter with which electrical energy, delivered via said probe shaft, is converted in shock-like manner into mechanical kinetic energy, said electro-hydraulic converter having a housing having a longitudinal direction, which accommodates a liquid chamber and a shock-transmitting element designed as a piston and moveable in said longitudinal direction of said housing from a proximal end position into a distal end position, said probe shaft having at least one delivery line for a liquid extending through the probe shaft and into said liquid chamber of said electro-hydraulic converter, said distal end position being defined by an abutment on said housing, toward which abutment a counter-abutment runs, which is arranged on said shock-transmitting element, said abutment and said counter-abutment being designed in such a way that, during a movement of said shock-transmitting element from said proximal end position to said distal end position, said counter-abutment comes directly into contact with said abutment, and said shock-transmitting element is moved back again to said proximal end position essentially by the impact of said counter-abutment on said abutment.

2. The device of claim 1, wherein said shock-transmitting element is held in said proximal end position by means of a holding mechanism, which withdraws essentially no kinetic energy from said shock-transmitting element during said movement from said proximal end position to said distal end position.

3. The device of claim 2, wherein said holding mechanism comprises a spring which is designed in such a way that a maximum possible spring travel of said spring is greater than a path of said shock-transmitting element between said proximal end position and said distal end position.

4. The device of claim 3, wherein said spring is a compression spring whose length is greater than said path of said shock-transmitting element between said proximal end position and said distal end position.

5. The device of claim 4, wherein said spring is arranged around a distal portion of said shock-transmitting element and having a distal end and a proximal end, said distal end bearing on said housing and said proximal end bearing on a shoulder of said shock-transmitting element, without lying in a running path of said counter-abutment.

6. The device of claim 2, wherein said holding mechanism holds said shock-transmitting element in said proximal end position by means of magnetic force.

7. The device of claim 1, wherein said counter-abutment is designed as a lateral projection which engages in a slide track in a wall of said housing, a distal end of said wall forming said abutment on said housing.

8. The device of claim 7, wherein said slide track is delimited at a proximal end in order to define said proximal end position of said shock-transmitting element.

9. The device of claim 7, wherein said lateral projection is formed by a pin which extends transversely through said shock-transmitting element and which at opposite ends engages in respective slide tracks in said wall of said housing.

10. The device of claim 1, wherein a stroke of said shock-transmitting element between said proximal end position and said distal end position lies in a range from approximately 0.2 to approximately 2 mm.

11. The device of claim 1, wherein a speed of said shock-transmitting element is at least 2 m/s.

12. The device of claim 1, wherein a speed of said shock-transmitting element is at least 15 m/s.

13. The device of claim 1, wherein a repetition frequency of said movement of said shock-transmitting element from said proximal end position to said distal end position is at least 2 Hz.

14. The device of claim 1, wherein a repetition frequency of said movement of said shock-transmitting element from said proximal end position to said distal end position is at least 15 Hz.

15. The device of claim 1, wherein said at least one delivery line is formed by at least one opening in a wall of said housing of said converter.

16. The device of claim 15, wherein said at least one opening is arranged distally from a portion of said shock-transmitting element which portion permits passage of liquid into said liquid chamber but prevents penetration of voltage sparks.

17. The device of claim 1, wherein said at least one delivery line is formed by at least one through-opening in said shock-transmitting element.

18. The device of claim 1, wherein said probe shaft is flexible.

19. The device of claim 1, wherein said probe head has, in its proximal area, a stiffening part.

20. The device of claim 19, wherein said probe head has said stiffening part along an entire length of said probe head.

21. The device of claim 1, wherein said probe head has a diameter of less than approximately 5 mm.

22. The device of claim 1, wherein said probe is integrated in a catheter.

23. The device of claim 22, wherein said catheter additionally has at least one lumen for at least one of a delivery and a removal of irrigation liquid.

24. The device of claim 22, wherein said catheter additionally has a lumen for passage of a miniaturized endoscope.

25. The device of claim 1, wherein an acoustic sensor is present which detects an acoustic signal of the ignition of said electro-hydraulic converter and of said impact of said shock-transmitting element on said substance.

* * * * *